US010308579B2

(12) United States Patent
Pandey et al.

(10) Patent No.: US 10,308,579 B2
(45) Date of Patent: Jun. 4, 2019

(54) METHOD OF BISPHENOL MANUFACTURE

(71) Applicant: SABIC Global Technologies B.V., Bergen op Zoom (NL)

(72) Inventors: Satish Chandra Pandey, Karnataka (IN); Gaurav Mediratta, Karnataka (IN); Alvaro Carrillo, Delmar, NY (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/759,919

(22) PCT Filed: Dec. 6, 2016

(86) PCT No.: PCT/US2016/065085
§ 371 (c)(1),
(2) Date: Mar. 14, 2018

(87) PCT Pub. No.: WO2017/100164
PCT Pub. Date: Jun. 15, 2017

(65) Prior Publication Data
US 2018/0265441 A1   Sep. 20, 2018

Related U.S. Application Data

(60) Provisional application No. 62/266,038, filed on Dec. 11, 2015.

(51) Int. Cl.
| C07C 37/20 | (2006.01) |
| C07C 39/16 | (2006.01) |
| H01M 10/6551 | (2014.01) |
| H01M 10/613 | (2014.01) |
| H01M 10/052 | (2010.01) |
| H01M 2/10 | (2006.01) |
| H01M 10/0525 | (2010.01) |
| H01M 10/0565 | (2010.01) |
| H01M 10/0587 | (2010.01) |

(52) U.S. Cl.
CPC .......... *C07C 37/20* (2013.01); *C07C 39/16* (2013.01); *H01M 2/1077* (2013.01); *H01M 10/052* (2013.01); *H01M 10/0525* (2013.01); *H01M 10/0565* (2013.01); *H01M 10/0587* (2013.01); *H01M 10/613* (2015.04); *H01M 10/6551* (2015.04); *C07C 2527/03* (2013.01); *H01M 2300/0065* (2013.01); *Y02T 10/7011* (2013.01)

(58) Field of Classification Search
CPC combination set(s) only.
See application file for complete search history.

(56) References Cited

U.S. PATENT DOCUMENTS

| 2,730,552 | A | * | 1/1956 | Williamson | ............ C07C 37/20 568/718 |
| 3,242,220 | A | | 3/1966 | Apel et al. | |
| 4,319,053 | A | | 3/1982 | Heuser et al. | |
| 4,348,542 | A | | 9/1982 | Serini et al. | |
| 4,387,251 | A | | 6/1983 | Meyer et al. | |
| 4,463,163 | A | | 7/1984 | Krishnan et al. | |
| 4,990,686 | A | | 2/1991 | Rauchschwalbe et al. | |
| 5,190,840 | A | | 3/1993 | Weiss et al. | |
| 5,304,688 | A | * | 4/1994 | Bowman | ................. C07C 37/20 568/717 |
| 5,914,431 | A | | 6/1999 | Fennhoff | |
| 6,872,859 | B2 | | 3/2005 | Perego et al. | |
| 9,174,904 | B1 | | 11/2015 | Chandra et al. | |
| 2012/0010433 | A1 | | 1/2012 | Munnich et al. | |

FOREIGN PATENT DOCUMENTS

| CN | 101863743 A | 10/2010 |
| JP | 2927880 B2 | 1/1992 |
| JP | 04956013 B2 | 6/2012 |

OTHER PUBLICATIONS

Machine generated English translation of CN 101863743, published Oct. 2010.*
Portada et al "Chiral Macrocyclic Bis(oxazoline) CuI Complexes—Structure/Stereoselectivity Relationships in Catalytic Cyclopropanations"; Eur. J. Org. Chem.; 2017; pp. 838-856.
Singh et al "Aromatics to bis-triguinane: a tandem oxidative dearomatization of bis-phenol, cycloaddition, photorearrangement and a rapid entry into carbocyclic framework of Xeromphalinone E"; Tetrahedron; 2014; 70; pp. 4485-4493.
Zhou et al "Structural Optimization and Biological Evaluation of Substituted Bisphenol A Derivatives as β-Amyloid Peptide Aggregation Inhibitors"; J. Med. Chem.; 2010; 53; pp. 5449-5466.
(Continued)

*Primary Examiner* — Rosalynd A Keys
(74) *Attorney, Agent, or Firm* — Cantor Colburn LLP

(57) ABSTRACT

An improved method of manufacture of a bisphenol comprises heating a monohydric phenol to a first temperature sufficient to melt the monohydric phenol; adding a carbonyl compound to 2.0-3.0 molar equivalents, based on the moles of carbonyl compound, of the monohydric phenol in the presence of catalytic amounts of an organosulfonic acid catalyst and a reaction promoter at a second temperature sufficient to maintain unreacted monohydric phenol in a molten state; increasing the temperature to a third temperature higher than the second temperature, and mixing for a time sufficient to produce the bisphenol in a yield of 80 to 100%, based on the amount of carbonyl compound; wherein mineral acids, Lewis acids, and ion exchange resins are not used. The method is applicable to the manufacture of 2,2-bis(3,5-dimethyl-4-hydroxyphenyl)propane, a useful intermediate for the manufacture of bi-functional poly(phenylene ether)s.

12 Claims, No Drawings

(56) References Cited

OTHER PUBLICATIONS

Ahn et al. "The Phase Behavior of Tetramethyl Bisphenol-A Polyarylate/Aliphatic Polyester Blends"; Journal of Polymer Science: Part B: Polymer Physics; 1998; vol. 36; pp. 201-212.
Curtis, "77. von Braun's "Diphenylcyclobutane Derivative": 6,6'-Dihydroxy-3,3,3',3-tetramethyl-1,1'-spirobi-indane and Related Compound"; Annalen; 1962; pp. 415-418.
English Abstract of JP2927880(B2).
International Search Report; International Application No. PCT/US2016/065085; International Filing Date Dec. 6, 2016; dated Mar. 6, 2017; 3 pages.
Liu et al. "Synthesis and Characterization of Readily Soluble Polyarylates Derived from Either 1,1-bis(4-hydroxyphenyl)-1-Phenylethane or Tetramethylbisphenol A and Aromatic Diacid Chlorides"; Journal of Applied Science; 2011; vol. 119; pp. 1923-1930.
Machine Translation for CN101863743 Dated Feb. 22, 2017.
Nava et al. "Functional Polymers and Sequential Copolymers by Phase Transfer Catalysis. 18. Synthesis and Characterization of α,ω-bis(2,6-dimethylphenol)-poly(2,6-dimethyl-1,4-phenylene oxide) and α,ω-bis(vinylbenzyl)-poly(2,6 dimethyl-1,4-phenylene oxide) Oligomers"; J. of Polymer Sci.: Part A: Polymer Chem; 1986: V. 24; 965-990.
Percec et al "Synthesis of a,w-bis(2,6-dimethylphenol)-poly(2,6-dimethyl-1,4-phenylene oxide) by phase transfer catalyzed polymerization of 4-bromo-2,6-dimethylphenol in the presence of 2,2-di(4-hydroxy-3,5-dimethylphenyl) propane"; Polymer Bulletin; 1990; 24; pp. 493-500.
Schnell; "Chemistry and Physics of Polycarbonates"; Chapter 4;1964; pp. 77-98.
Written Opinion of the International Searching Authority; International Application No. PCT/US2016/065085; International Filing Date Dec. 6, 2016; dated Mar. 6, 2017; 8 pages.

\* cited by examiner

METHOD OF BISPHENOL MANUFACTURE

CROSS REFERENCE TO RELATED APPLICATIONS

This application is a National Stage application of PCT/US16/065085 filed Dec. 6, 2016, which claims the benefit of U.S. Provisional Application No. 62/266,038, filed Dec. 11, 2015, both of which are incorporated by reference in their entirety herein.

BACKGROUND OF THE INVENTION

Bisphenols are useful chemical intermediates for the preparation of polymers, for example epoxy resins, polycarbonates, and bifunctional poly(phenylene ether)s. Of particular interest are bisphenols in which the two monohydric phenol groups are linked by an aliphatic carbon atom. The divalent linking group for two monohydric phenols can be, for example, methylene (as in bisphenol F), ethylidene (as in bisphenol E), or 2,2-propylidene (as in bisphenol A).

Bisphenols can be made by reaction of a carbonyl compound with two or more equivalents of a monohydric phenol using an acid or base catalyst. Mineral acid catalysts, for example hydrochloric acid or sulfuric acid, can be used. However corrosion of metal reactors and fittings can be a major problem when hydrochloric acid is used. Moreover, the yield of bisphenol obtained using hydrochloric acid can be low. With sulfuric acid, sulfonated impurities can be formed as byproducts, which reduces the yield and purity of bisphenol. The bisphenols so made may not be suitable as intermediates without purification to remove sulfonated byproducts. Acid-functional ion exchange resins can also be used. However there is room for improvement in the yield and purity of the bisphenols produced using acid-functional ion exchange resins as well. An improved method for manufacture of bisphenols, which does not suffer from the drawbacks associated with the use of mineral acid catalysts or acid-functional organic ion exchange resins, and which produces bisphenols in higher yield and purity, and at a lower cost, is desirable.

BRIEF SUMMARY OF EMBODIMENTS OF THE INVENTION

An improved method of manufacture of a bisphenol of chemical structure:

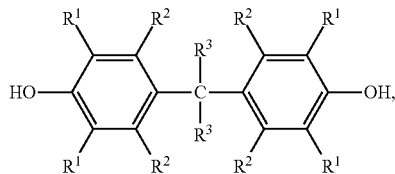

wherein each $R^1$ is independently selected from the group consisting of hydrogen, halogen, methoxy, and $C_{1-12}$ hydrocarbyl provided that the hydrocarbyl group is not tertiary hydrocarbyl; each $R^2$ is independently selected from the group consisting of hydrogen, halogen, and $C_{1-12}$ hydrocarbyl provided that the hydrocarbyl group is not tertiary hydrocarbyl, and each $R^3$ is independently selected from the group consisting of hydrogen, halogen, and $C_{1-11}$ hydrocarbyl, comprises: heating a monohydric phenol of chemical structure:

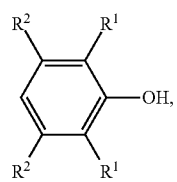

wherein $R^1$ and $R^2$ are as defined above, to a first temperature sufficient to melt the monohydric phenol; adding a carbonyl compound of chemical structure:

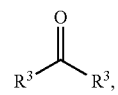

wherein $R^3$ is a defined above, to 2.0-3.0 molar equivalents, based on the moles of carbonyl compound, of the monohydric phenol in the presence of catalytic amounts of an organosulfonic acid catalyst and a reaction promoter at a second temperature sufficient to maintain unreacted monohydric phenol in a molten state; increasing the temperature to a third temperature higher than the second temperature, and mixing for a time sufficient to produce the bisphenol in a yield of 80 to 100%, based on the amount of carbonyl compound; wherein mineral acids, Lewis acids, and ion exchange resins are not used.

In some embodiments, the method is directed to the manufacture of a bisphenol of chemical structure:

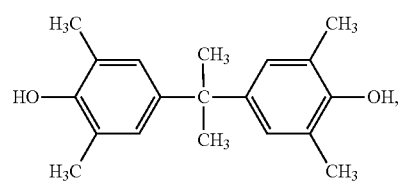 [SMILES: Cc1cc(C(C)(C)c2cc(C)c(O)c(C)c2)cc(C)c1O]

wherein the method comprises heating 2,6-dimethylphenol to a first temperature sufficient to melt the 2,6-dimethylphenol; adding acetone to 2.0-2.5 molar equivalents, based on the moles of acetone, of the 2,6-dimethylphenol, in the presence of catalytic amounts of an organosulfonic acid catalyst and a reaction promoter at a second temperature of 40 to 50° C.; increasing the temperature to a third temperature of 70 to 80° C., and mixing for a time sufficient to produce the bisphenol in a yield of 80 to 100%, based on the amount of carbonyl compound; wherein mineral acids, Lewis acids, and ion exchange resins are not used.

These and other embodiments are described in detail below.

DETAILED DESCRIPTION OF THE INVENTION

A method of manufacture of a bisphenol using organosulfonic acid catalysts results in increased yield and purity compared to methods using mineral acids, Lewis acids, or acid-functional cationic ion exchange resins. The method produces bisphenol in high yield and purity, and significantly reduces the manufacturing cost. The method is applicable to the manufacture of 2,2-bis(3,5-dimethyl-4-hydroxyphenyl)propane (TMBPA), which is useful in the manufacture of bifunctional poly(phenylene ether)s.

The method is directed to the manufacture of bisphenols of chemical structure:

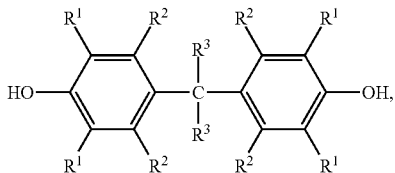

wherein each $R^1$ is independently selected from the group consisting of hydrogen, halogen, methoxy, and $C_{1-12}$ hydrocarbyl provided that the hydrocarbyl group is not tertiary hydrocarbyl; each $R^2$ is independently selected from the group consisting of hydrogen, halogen, and $C_{1-12}$ hydrocarbyl provided that the hydrocarbyl group is not tertiary hydrocarbyl, and each $R^3$ is independently selected from the group consisting of hydrogen, halogen, and $C_{1-11}$ hydrocarbyl. The method comprises heating a monohydric phenol of chemical structure:

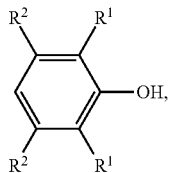

wherein $R^1$ and $R^2$ are as defined above, to a first temperature sufficient to melt the monohydric phenol; adding a carbonyl compound of chemical structure:

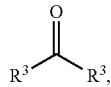

wherein $R^3$ is a defined above, to 2.0 to 3.0 molar equivalents, based on the moles of carbonyl compound, of the monohydric phenol in the presence of catalytic amounts of an organosulfonic acid catalyst and a reaction promoter at a second temperature sufficient to maintain unreacted monohydric phenol in a molten state; increasing the temperature to a third temperature higher than the second temperature, and mixing for a time sufficient to produce the bisphenol in a yield of 80 to 100%, based on the amount of carbonyl compound; wherein mineral acids, Lewis acids, and ion exchange resins are not used. In some embodiments, each occurrence of $R^1$ and $R^3$ is methyl, and each occurrence of $R^2$ is hydrogen.

The bisphenol is characterized by a 1-carbon atom linkage of the two phenols in the para positions. The linking group is a divalent alkylidene group, and can be for, example, methylidene, ethylidene, propylidene, cyclohexylidene, benzylidene, or phenylethylidene. Examples of methylidene-linked bisphenols include bis(4-hydroxyphenyl)methane (Bisphenol F), bis(4-hydroxy-2,6-dimethyl-3-methoxyphenyl)methane, bis(3,5-dimethyl-4-hydroxyphenyl) methane, bis(3-methyl-4-hydroxyphenyl)methane, bis(3-methyl-4-hydroxyphenyl)methane, bis(3,5-dimethyl-4-hydroxyphenyl)methane, and bis(4-hydroxy-5-nitrophenyl) methane. Examples of ethylidene-linked bisphenols include 1,1-bis(4-hydroxyphenyl)ethanen (Bisphenol E), 1,1-bis(3-methyl-4-hydroxyphenyeethane, 1,1-bis(3,5-dimethyl-4-hydroxyphenyl)ethane, 1,1-bis-(2,5-dimethyl-4-hydroxyphenyl)ethane; 1,1-bis(3-chloro-4-hydroxyphenyl)ethane, and 1,1-bis(2-chloro-4-hydroxyphenyl)ethane.

Examples of propylidene-linked bisphenols include 2,2-bis(3-methyl-4-hydroxyphenyl)propane, 2,2-bis(3-isopropyl-4-hydroxyphenyl)propane (Bisphenol G), 2,2-bis(3,5-dimethyl-4-hydroxyphenyl)propane, 2,2-bis(3-phenyl-4-hydroxyphenyl)propane (Bisphenol PH), 2,2-bis(3-methyl-4-hydroxy-5-phenylphenyl)propane, 2,2-bis(3,5-diphenyl-4-hydroxyphenyl)propane, 2,2-bis(2,3,6-trimethylphenyl) propane, 2,2-bis(3,5-dichloro-4-hydroxyphenyl)propane, 2,2-bis(3-bromo-4-hydroxyphenyl)propane, 2,2-bis(3,5-dibromo-4-hydroxyphenyl)propane(Tetrabromobisphenol A), and 2,2-bis(2-allyl-4-hydroxyphenyl)propane (diallyl Bisphenol A).

Examples of cyclohexylidene-linked bisphenols include 1,1-bis(4-hydroxyphenyl)cyclohexane(Bisphenol Z), 1,1-bis(3,5-dibromo-4-hydroxyphenyl)cyclohexane, 1,1-bis(3,5-dimethyl-4-hydroxyphenyl)cyclohexane, and bis(3-methyl-4-hydroxyphenyl)cyclohexane. Examples of 1-phenylethylidene-linked bisphenols include 1,1-bis(4-hydroxyphenyl)-1-phenylethane (Bisphenol AP), 1,1-bis(3,5-dimethyl-4-hydroxyphenyl)-1-phenylethane, 1,1-bis(3-chloro-4-hydroxyphenyl)-1-phenylethane, and 1,1-bis(3-methyl-4-hydroxyphenyl)-1-phenylethane.

Examples of other alkylidene-linked bisphenols include 2,2-bis(4-hydroxyphenyl)butane (Bisphenol B), 2,2-bis(4-hydroxyphenyl)pentane, 2,2-bis(4-hydroxy-3,5-dimethylphenyl)pentane, 2,2-bis(3-methyl-4-hydroxyphenyl)pentane, 3,3-bis(4-hydroxyphenyl)pentane, 2,2-bis(4-hydroxy-3,5-dimethyl phenyl)hexane, 2,2-bis(3-methyl-4-hydroxyphenyl)hexane, 2,2-bis-(4-hydroxyphenyl)heptane, bis(4-hydroxyphenyl)phenylmethane, bis(3-methyl-4-hydroxyphenyl)phenylmethane, bis(4-hydroxy-3,5-dimethylphenyl)phenylmethane, 2,2-bis(4-hydroxy-3,5-dimethyl phenyl)-1-phenylpropane, 2,2-bis(3-methyl-4-hydroxyphenyl)-1-phenylpropane, bis(3-methyl-4-hydroxyphenyl)cyclohexylmethane, and 1,1-bis(4-hydroxy-3,5-dimethylphenyl)cyclohexylmethane, 1,1-bis(4-hydroxyphenyl)-3,3,5-trimethylcyclohexane (Bisphenol TMC), 2,2-bis(4-hydroxyphenyl)-1-phenylpropane, 2,2-bis(4-hydroxyphenyl)hexafluoropropane (Bisphenol AF), and bis (4-hydroxyphenyl)diphenylmethane (Bisphenol BP). In some embodiments, the bisphenol is 2,2-bis(3,5-tetramethyl-4-hydroxyphenyl)propane, which has the chemical structure:

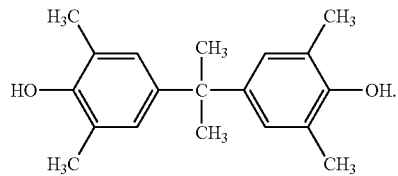 [SMILES: Cc1cc(C(C)(C)c2cc(C)c(O)c(C)c2)cc(C)c1O]

The monohydric phenol is unsubstituted in the para position, so that it can react with carbonyl compound to form a bisphenol where the two monohydric phenols are linked by a divalent alkylidene group at the para positions. Examples of monohydric phenols include phenol, 2-methylphenol, 2-isopropylphenol, 3-allylphenol, 2-chlorophenol, 3-chlorophenol, 2-bromophenol, 2-nitrophenol, 2,6-dibromophenol, 2,6-dimethylphenol, 2,3,6-trimethylphenol, 2,5-dimethylphenol, 2-methoxy-3,5-dimethylphenol, 2-phenylphenol, 2-methyl-6-phenylphenol, and combinations thereof. In some embodiments, the monohydric phenol is selected from phenol, 2-methylphenol, 2,6-dimethylphenol, 2,3,6-trimethylphenol, 2-methyl-6-phenylphenol, and combinations thereof. In some embodiments, the monohydric phenol consists of 2,6-dimethylphenol.

In some embodiments, the carbonyl compound is formaldehyde, a $C_{2-12}$ aldehyde, or $C_{3-12}$ ketone. The carbonyl compound can be, for example, formaldehyde, acetone, butanone (methyl ethyl ketone), 2-pentanone, 3-pentanone, 2-heptanone, cyclohexanone, 3,3,5-trimethylcyclohexanone, 1-formylcyclohexane, benzaldehyde, acetophenone, benzophenone, phenylacetone, hexafluoroacetone, and combinations thereof. In some embodiments, the carbonyl compound is selected from formaldehyde, acetaldehyde, acetone, cyclohexanone, and combinations thereof. In some embodiments, the carbonyl compound consists of acetone. The method comprises adding the carbonyl compound to 2.0 to 3.0 molar equivalents, based on the moles of carbonyl compound, of monohydric phenol. Within this range, the molar equivalents of monohydric phenol can be greater than or equal to 2.0 to less than or equal to 2.5, 2.4, 2.3, 2.2, 2.1, or 2.05. In some embodiments the molar equivalents of carbonyl compound is 2.0 to 2.05.

Advantageously, the bisphenol is produced in a yield of 80 to 100%, based on the amount of carbonyl compound, the limiting reagent. Within this range, the yield can be greater than or equal to 80 to less than or equal to 95%, 90%, 87%, 85%, or 83%. In some embodiments, the yield is 80 to 83%. Advantageously, the bisphenol is obtained in a purity of greater than or equal to 99 weight percent. In some embodiments where the bisphenol is 2,2-(3,5-dimethyl-4-hydroxyphenyl)propane, the purity can be 99 to 99 to 100 percent by weight, specifically 99.0 to 99.5 percent by weight.

The method employs an organosulfonic acid catalyst. Examples of organosulfonic acid catalysts include dodecylbenzene sulfonic acid (DBSA), ethylbenzene sulfonic acid, butylnaphthalene sulfonic acid, dinonylnaphthalene sulfonic acid (DNNSA), toluene sulfonic acid (TSA), chlorobenzene sulfonic acid, xylene sulfonic acid, cumene sulfonic acid, phenol sulfonic acid, and combinations thereof. In some embodiments, the organosulfonic acid catalyst is selected from dodecylbenzene sulfonic acid, ethylbenzene sulfonic acid, butylnaphthalene sulfonic acid, and combinations thereof. The amount of acid catalyst can be 0.001 to 0.5 molar equivalent, based on the moles of carbonyl compound. Within this range, the amount can be greater than or equal to 0.005, 0.01, 0.05, or 0.1 molar equivalent and less than or equal to 0.4 or 0.3 molar equivalent. In some embodiments, the amount of organosulfonic acid catalyst is 0.05 to 0.4 molar equivalent.

The method employs a reaction promoter that is an ionizable compound of divalent sulfur, for example, sulfur dichloride, sodium thiosulfate, hydrogen sulfide, sodium sulfide, thioacetic acid, 3-mercaptopropionic acid (3-MPA), 4-mercaptobutyric acid, 2-mercaptoisobutryric acid, 3-mercaptoisobutyric acid, thioglycolic acid, mercaptans, thiophenols, mercaptoalkane sulfonic acids, hydroxyalkyl mercaptans, and combinations thereof. In some embodiments, the reaction promoter is selected from 3-mercaptopropionic acid (3-MPA), 4-mercaptobutyric acid, 2-mercaptoisobutryric acid, 3-mercaptoisobutyric acid, and combinations thereof. The amount of acid promoter can be 0.001 to 0.5 molar equivalent, based on the moles of carbonyl compound. Within this range, the amount can be greater than or equal to 0.005, 0.01, 0.03, 0.05, or 0.1 molar equivalent and less than or equal to 0.4, 0.3, or 0.2 molar equivalent. In some embodiments, the amount of reaction promoter is 0.03 to 0.2 molar equivalent. 9. In some embodiments, the organosulfonic acid comprises, based on the moles of carbonyl compound, 0.05 to 0.4 molar equivalent of dodecylbenzene sulfonic acid and the reaction promoter comprises 0.03 to 0.2 molar equivalent of 3-mercaptopropionic acid.

The method employs an organosulfonic acid catalyst and a reaction promoter as defined herein. However other catalysts, such as mineral acids, Lewis acids, and ion exchange resins, are not used. Mineral acids are inorganic acids, i.e. acids that do not contain carbon atoms. Examples of mineral acids include hydrogen chloride, hydrogen bromide, hydrogen fluoride, phosphoric acid, sulfuric acid, and combinations thereof. Examples of Lewis acids include boron fluoride, aluminum chloride, phosphorous halides, and combinations thereof.

Ion exchange resins are composed of a three-dimensional, cross-linked polymer matrix having a relatively uniform distribution of ionizable functional groups throughout the polymer matrix. The ionizable functional group can be added by reaction of polymers, e.g. sulfonation of polystyrene, or by copolymerizing ionizable monomers with non-ionic monomers. The cross-linking provides a relatively insoluble and rigid material. The ion exchange resin can be a cation exchange resin, for example a strong acid ion exchange resin functionalized with sulfonic acid groups, or a weakly acidic cation exchange resin functionalized with carboxylic acid groups. An example of a cationic exchange resin is divinylbenzene cross-linked polystyrene sulfonic acid. Cationic exchange resins are commercially available under the DOWEX™, AMBERLITE™, DUOLITE™, LEWATIT™, and PUROLITE™ tradenames.

The method comprises heating the monohydric phenol to a first temperature sufficient to melt the monohydric phenol, and adding a carbonyl compound at a second temperature sufficient to maintain unreacted monohydric phenol in a molten state. For example, when the monohydric phenol is 2,6-dimethylphenol, with a melting point of 43-48° C., the second temperature can be 30 to 100° C. Within this range the second temperature can be greater than or equal to 32, 34, 36, 38, 40 to less than or equal to 90, 80, 70, 60, 50, or 45° C. In some embodiments, the second temperature is 40 to 50° C., specifically 40 to 45° C., more specifically 41 to 43° C. The first temperature can be the same or different from the second temperature. In some embodiments, the first temperature is higher than the second temperature to facilitate melting of the monohydric phenol. The adding can be done for 30 minutes to 12 hours. Within this time, the adding can be done in greater than or equal to 1, 2, or 3 hours to less than or equal to 10, 9, 8, 7, or 6 hours. In some embodiments, the adding is done for 4 to 6 hours.

The method also comprises increasing the temperature to a third temperature higher than the second temperature, and mixing for a time sufficient to produce the bisphenol in a yield of 80 to 100%, based on the amount of carbonyl compound. The temperature can be increased before or after addition of carbonyl compound is complete. The third temperature can be 40 to 150° C. Within this range, the third temperature can be greater than or equal to 50, 60, or 70° C. to less than or equal to 140, 120, 100, 90, or 80° C. The third temperature can be optimized based on reaction time and yield. If the third temperature is too low, the reaction time can be too long to be economical. If the third temperature is too high, side reactions leading to undesired impurities can occur, and product yield and purity reduced. Also, for safety reasons, it is desirable that the third temperature be below the flash point of the monohydric phenol. For example, when the first monohydric phenol is 2,6-dimethylphenol, which has a flash point of 86° C., the third temperature can be 50 to 80° C., specifically greater than or equal to 60, 65, or 70° C. to less than or equal to 80° C. In some embodiments, the third temperature is 70 to 80° C.

The mixing can be done for 1 to 48 hours. Within this range, the mixing can be done for greater than or equal to 3, 6, 9, 12, 15, or 18 hours to less than or equal to 42, 36, 30, or 24 hours. In some embodiments, the mixing is done for 18 to 24 hours. In some embodiments, when the monohydric phenol is 2,6-dimethylphenol, the carbonyl compound is acetone, and the bisphenol is 2,2-bis(3,5-dimethyl-4-hydroxyphenyl)propane, the adding is done for 3 to 6 hours and the mixing is done for 18 to 30 hours.

Some carbonyl compounds are relatively low boiling, for example, formaldehyde, acetaldehyde, and acetone, which having boiling points of −19, 20, and 56° C., respectively. However adding the carbonyl compound is done at a second temperature sufficient to maintain unreacted monohydric phenol in a molten state, which can be at or near the boiling point of the carbonyl compound. Thus evaporation of the carbonyl compound during addition can occur, reducing yield. In order to address this issue, the inventors have found that evaporative loss can be reduced by addition of the carbonyl compound below the surface of the molten monohydric phenol, so that is has an opportunity to dissolve in the molten monohydric phenol before evaporation into the reaction vessel headspace. Advantageously, addition of the carbonyl compound below the surface of the molten monohydric phenol can reduce the amount of carbonyl compound in the vapor phase of the reaction vessel and thereby reduce the risk of ignition of the carbonyl compound when the first temperature is above the flash point of the carbonyl compound. Thus in some embodiments, the carbonyl compound is added below a surface of molten monohydric phenol.

In some embodiments, the carbonyl compound is cooled to 5 to 10° C. prior to adding it to the monohydric phenol in order to minimize evaporative loss of the carbonyl compound. This also provides some cooling to the reaction mixture, as the reaction of carbonyl compound with monohydric phenol is exothermic.

In the method, carbonyl compound is added to 2.0 to 3.0 molar equivalents, based on the moles of carbonyl compound, of the monohydric phenol in the presence of catalytic amounts of an organosulfonic acid catalyst and a reaction promoter at the second temperature. In some embodiments, the organosulfonic acid catalyst is added to the monohydric phenol simultaneously with the carbonyl compound, but as a separate stream, i.e. the organosulfonic acid and carbonyl compound are not pre-mixed and added together as a single stream.

If the organosulfonic acid catalyst is all added to the monohydric phenol prior to addition of carbonyl compound, which results in a larger relative concentration of organosulfonic acid catalyst to carbonyl compound during the addition of carbonyl compound, undesirable acid-catalyzed side reactions of the carbonyl compound can occur. Also, if the organosulfonic acid catalyst is mixed with the carbonyl compound prior to addition of a mixture of the two, the long contact time between organosulfonic acid catalyst and carbonyl compound in the absence of monohydric phenol prior to addition can also favor acid-catalyzed side reactions of the carbonyl compound. For example, when the carbonyl compound has an alpha-hydrogen, i.e. an ionizable hydrogen on the carbon atom alpha to the carbonyl carbon, for example acetone, self-reaction of the carbonyl compound can take place (aldol condensation), which results in reduced yield of the bisphenol. Advantageously, these side reactions are minimized when the organosulfonic acid catalyst is added to the monohydric phenol simultaneously with the carbonyl compound, but as a separate stream.

The organosulfonic acids are generally high boiling liquids or solids. Therefore evaporative loss in the headspace of the reactions vessel is not an issue, and the organosulfonic acid can be added from above the surface of the molten monohydric phenol. Thus in some embodiments, the carbonyl compound is added below the surface, and the organosulfonic acid is simultaneously added from above the surface, of the molten monohydric phenol.

The method can be conducted neat, that is in the absence of solvents. The method can also be conducted in the presence of a solvent. Factors including cost, health and safety hazards, solubility of the monohydric phenol, carbonyl compound, bisphenol, organosulfonic acid catalyst, and reaction promoter in the solvent, inertness of the solvent to the reactants, and ease of solvent recycling can be considered when choosing a solvent. The solvent can be, for example, a non-polar solvent, such as benzene, toluene, ethylbenzene, cumene, xylenes, mesitylene, tetralin, chlorobenzene, dichlorobenzenes, chloroform, or combinations thereof.

The bisphenol can be a solid at room temperature. For example, 2,2-bis(3,5-dimethyl-4-hydroxyphenyl)propane has a melting point of 162-165° C. When the bisphenol is a solid, it can be isolated in pure form by recrystallization from a solvent that dissolves the impurities, but which is a non-solvent for the bisphenol at room temperature or below. For example, TMBPA can be isolated by diluting the reaction mass with toluene with stirring to dissolve impurities, cooling to 10° C. to precipitate the TMBPA, isolating it by filtration, washing it with more toluene, and drying.

As mentioned above, the method is applicable to the manufacture of 2,2-bis(3,5-dimethyl-4-hydroxyphenyl)propane (TMBPA), which is useful in the manufacture of bifunctional poly(phenylene ether)s with improved properties relative to monofunctional poly(phenylene ether)s. Thus in some embodiments, the method is directed to the manufacture of a bisphenol of chemical structure:

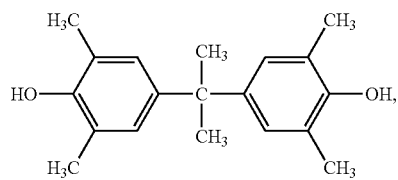

wherein the method comprises heating 2,6-dimethylphenol to a first temperature sufficient to melt the 2,6-dimethylphenol; adding acetone to 2.0-2.5 molar equivalents, based on the moles of acetone, of the 2,6-dimethylphenol, in the presence of catalytic amounts of an organosulfonic acid catalyst and a reaction promoter at a second temperature of 40 to 50° C.; increasing the temperature to a third temperature of 70 to 80° C., and mixing for a time sufficient to produce the bisphenol in a yield of 80 to 100%, based on the amount of carbonyl compound; wherein mineral acids, Lewis acids, and ion exchange resins are not used.

A method of manufacture of bisphenols has been disclosed herein. The method does not suffer from the drawbacks associated with the use of mineral acid catalysts or acid-functional ion exchange resins, and produces bisphenols in high yield and purity at a lower manufacturing cost due to lower monohydric phenol consumption. The amount of monohydric phenol is limited to 2.0 to 3.0 molar equivalents, based on the moles of carbonyl compound, and the carbonyl compound is added to the monohydric phenol in the presence of catalytic amounts of organosulfonic acid catalyst and reaction promoter. The method is applicable to the manufacture of 2,2-bis(3,5-dimethyl-4-hydroxyphenyl)propane, a useful intermediate for the manufacture of bifunctional poly(phenylene ether)s.

The invention includes at least the following embodiments.

Embodiment 1: A method of manufacture of a bisphenol of chemical structure:

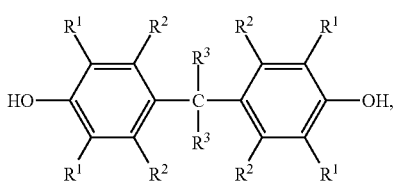

wherein each $R^1$ is independently selected from the group consisting of hydrogen, halogen, methoxy, and $C_{1-12}$ hydrocarbyl provided that the hydrocarbyl group is not tertiary hydrocarbyl; each $R^2$ is independently selected from the group consisting of hydrogen, halogen, and $C_{1-12}$ hydrocarbyl provided that the hydrocarbyl group is not tertiary hydrocarbyl, and each $R^3$ is independently selected from the group consisting of hydrogen, halogen, and $C_{1-11}$ hydrocarbyl, the method comprising: heating a monohydric phenol of chemical structure:

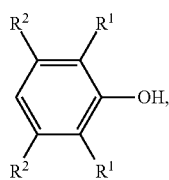

wherein $R^1$ and $R^2$ are as defined above, to a first temperature sufficient to melt the monohydric phenol; adding a carbonyl compound of chemical structure:

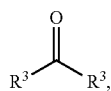

wherein $R^3$ is a defined above, to 2.0 to 3.0 molar equivalents, based on the moles of carbonyl compound, of the monohydric phenol in the presence of catalytic amounts of an organosulfonic acid catalyst and a reaction promoter at a second temperature sufficient to maintain unreacted monohydric phenol in a molten state; increasing the temperature to a third temperature higher than the second temperature, and mixing for a time sufficient to produce the bisphenol in a yield of 80 to 100%, based on the amount of carbonyl compound; wherein mineral acids, Lewis acids, and ion exchange resins are not used.

Embodiment 2. The method of embodiment 1, wherein the monohydric phenol is selected from phenol, 2-methylphenol, 2,6-dimethylphenol, 2,3,6-trimethylphenol, 2-methyl-6-phenylphenol, and combinations thereof.

Embodiment 3. The method of embodiment 1 or 2, wherein the carbonyl compound is formaldehyde, a $C_{2-12}$ aldehyde, or $C_{3-12}$ ketone.

Embodiment 4. The method of any of embodiments 1 to 3, wherein the carbonyl compound is selected from formaldehyde, acetaldehyde, acetone, cyclohexanone, and combinations thereof.

Embodiment 5. The method of any of embodiments 1 to 4, wherein the organosulfonic acid catalyst is selected from dodecylbenzene sulfonic acid, ethylbenzene sulfonic acid, butylnaphthalene sulfonic acid, and combinations thereof.

Embodiment 6. The method of any of embodiments 1 to 5, wherein the reaction promoter is selected from 3-mercaptopropionic acid (3-MPA), 4-mercaptobutyric acid, 2-mercaptoisobutyric acid, 3-mercaptoisobutyric acid, and combinations thereof.

Embodiment 7. The method of any of embodiments 1 to 6, wherein the carbonyl compound is added below a surface of molten monohydric phenol.

Embodiment 8. The method of any of embodiments 1 to 7, wherein the organosulfonic acid catalyst is added simultaneously with the carbonyl compound, but as a separate stream.

Embodiment 9. The method of any of claims 1 to 8, wherein the organosulfonic acid comprises, based on the moles of carbonyl compound, 0.05 to 0.4 molar equivalent of dodecylbenzene sulfonic acid and the reaction promoter comprises 0.03 to 0.2 molar equivalent of 3-mercaptopropionic acid.

Embodiment 10. The method of any of embodiments 1 to 9, wherein each occurrence of $R^1$ and $R^3$ is methyl, and each occurrence of $R^2$ is hydrogen.

Embodiment 11. The method of any of embodiments 1 to 10, wherein the bisphenol is of chemical structure:

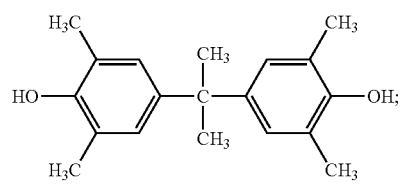 [SMILES: Cc1cc(C(C)(C)c2cc(C)c(O)c(C)c2)cc(C)c1O]

and wherein the method comprises: addition of acetone to 2.0 to 2.5 molar equivalents of 2,6-dimethylphenol in the presence of catalytic amounts of an organosulfonic acid catalyst and a reaction promoter at a second temperature of 40 to 50° C.; and increasing the temperature to a third temperature of 70 to 80° C. and mixing.

Embodiment 12. The method of embodiment 11, wherein the adding is done for 3 to 6 hours; and the mixing is done for 18 to 36 hours.

The invention is further illustrated by the following non-limiting examples.

EXAMPLE 1

Chemical abbreviations used herein are described in Table 1.

TABLE 1

| Component | Description |
|---|---|
| DMP | 2,6-Dimethylphenol (2,6-xylenol); C.A.S. Reg. No. 576, 26-1, 99.6 wt % purity by gas chromatography. |
| TMBPA | 2,2-Bis(3,5-dimethyl-4-hydroxyphenyl)propane; C.A.S. Reg. No. 203578-30-7. |
| 3-MPA | 3-Mercaptopropionic acid; C.A.S. Reg. No. 107-96-0. |
| DBSA | Dodecylbenzesulfonic acid; C.A.S. Reg. No. 85536-14-7. |

Reactants, catalysts, and amounts thereof utilized for the preparation of 2,2-bis(3,5-dimethyl-4-hydroxyphenyl)propane are summarized in Table 2.

TABLE 2

| Raw Material | Mol. Wt. (g/mol) | Density (g/mL) | Quantity (g) | Quantity (mL) | Quantity (mol) | Mole Ratio |
|---|---|---|---|---|---|---|
| Acetone | 58.10 | 0.79 | 12.00 | 15.19 | 0.206 | 1.00 |
| DMP | 122.20 | 1.01 | 51.74 | 51.23 | 0.423 | 2.05 |
| 3-MPA | 106.14 | 1.22 | 4.17 | 3.42 | 0.04 | 0.19 |
| DBSA | 326.49 | 1 | 11.46 | 11.46 | 0.04 | 0.17 |
| Toluene | 92.14 | 0.87 | 172.41 | 199 | a | a | a Not applicable

The specified amounts of DMP (51.74 g, 0.423 moles) and 3-MPA were charged to a three-necked round bottomed flask equipped with a thermometer and mechanical stirrer, and heated to 49° C. to melt the DMP. DBSA was added drop-wise from the top of the flask, and cold (5-10° C.) acetone (12.0 g, 0.206 moles, for a DMP to acetone mole ratio of 2.05:1) was simultaneously added via a dip tube below the surface of the melt with stirring. After 10% of the acetone was added, the temperature was reduced to 42° C., at which temperature the DMP remained molten. The addition was continued over a period of 4 to 5 hrs. at 42° C. After the addition of acetone was complete, the temperature was increased to 75° C. and maintained at 75° C. for 24 hrs. with stirring. The resulting slurry was diluted with toluene (108 mL) with stirring. After stirring for 1 hr., the slurry was cooled to 10° C. The solid was isolated by filtration, washed with 72 mL of cold (10° C.) toluene, and dried in an oven for 6 hrs. at 65° C. to give 47.9 g of TMBPA in 81% yield based on acetone as limiting reagent, and in 99.3% purity, based on gas chromatography (GC) and high-performance liquid chromatograph (HPLC).

The yield of 81% is an isolated yield. It does not take into account any TMBPA present in the toluene mother liquor after filtration and toluene washing of the product. Higher isolated yields are possible if a second crop of TMBPA crystals is isolated from the toluene mother liquor.

COMPARATIVE EXAMPLE 1

DMP (153 g, 1.25 moles) and 3-MPA (10.0 g) were charged to a 1-liter three-necked round bottomed flask equipped with a thermometer and mechanical stirrer, and heated to 35° C. DBSA (27 g) and acetone (29 g, 0.499 mole, for a DMP to acetone mole ratio of 2.50:1) were simultaneously added drop-wise from the top of the flask over a period of 2 hrs. with stirring. After the addition of acetone was complete, the temperature was increased to 75° C. and maintained at 75° C. for 24 hrs. with stirring. The resulting slurry was diluted with toluene (300 mL) with stirring. After stirring for 1 hr., the slurry was cooled to 10° C. The solid was isolated by filtration, washed with 200 mL of cold (10° C.) toluene, and dried in an oven at 70° C. overnight to give TMBPA in 62% yield based on acetone as limiting reagent and in >99.0% purity by HPLC.

Advantageously, the inventive method illustrated by Example 1 provided a high yield and minimized the use of DMP relative to Comparative Example 1, which results in reduced cost for the TMBPA made by the method. The differences between the methods are illustrated in Table 3. As can be seen from Table 3, the first temperature is sufficiently high in Example 1 to maintain the DMP in a molten state, which is thought to increase its reactivity relative to the solid DMP of Comparative Example 1. Also, the acetone is added below the surface of the reaction mixture in Example 1, which is thought to reduce evaporative loss of acetone in the vapor phase that occurs when it is added above the surface as in Comparative Example 1. Advantageously, the high yield of Example 1 is obtained at a reduced DMP to acetone ratio (2.05 vs. 2.50), which significantly reduces the cost of the process.

TABLE 3

| Parameter | Comp. Ex. 1 | Ex. 1 |
|---|---|---|
| Ratio of DMP:acetone | 2.50 | 2.05:1 |
| Second temperature$^a$ | 30° C. | 42° C. |
| State of DMP | Solid | Molten |
| Mode of acetone addition | Addition from top @ 0.24 g/min. | Addition from bottom @ 0.04 to 0.05 g/min. |
| Third temperature$^b$ | 75° C. | 75° C. |
| Yield | 62% | 81% |
| Purity | ≥99% | ≥99% |

$^a$Temperature of acetone addition.
$^b$Temperature for hold period after acetone addition.

COMPARATIVE EXAMPLE 2

DMP (52.79 g, 0.432 mole) and 3-MPA (3.47 g) were charged to a three-necked round bottomed flask equipped with a thermometer and mechanical stirrer, and heated to 35° C. DBSA (9.55 g) and acetone (10.0 g, 0.172 mole, for a DMP to acetone mole ratio of 2.51:1) were simultaneously added drop-wise from the top of the flask over a period of 2 hrs. with stirring. After the addition of acetone was complete, the temperature was increased to 75° C. and maintained at 75° C. for 24 hrs. with stirring. The product was isolated as in Comparative Example 1 to give 34.41 g of TMBPA (70.4% yield).

COMPARATIVE EXAMPLE 3

Comparative Example 2 was repeated, except for the following changes. The DMP and 3-MPA were heated to 48° C. instead of 35° C. After 10% of the acetone was added, the temperature was reduced to 42° C. The acetone was added via a dip tube below the surface of the melt. The yield of TMBPA was increased from 70.4% to 75.0%. This comparative example illustrates the improvement in yield obtained by adding the acetone at a second temperature at which the DMP is molten, and by adding the acetone below the surface of the melt.

COMPARATIVE EXAMPLE 4

Comparative Example 2 was repeated, except twice the amount of 3-MPA was used (6.94 g, 0.38 molar equivalents based on acetone). The yield of TMBPA was increased from 70.4% to 76.0%.

As used herein, the terms "a" and "an" do not denote a limitation of quantity, but rather the presence of at least one of the referenced items. Recitation of ranges of values are merely intended to serve as a shorthand method of referring individually to each separate value falling within the range, unless otherwise indicated herein, and each separate value is incorporated into this specification as if it were individually recited. Thus each range disclosed herein constitutes a disclosure of any sub-range falling within the disclosed range. Disclosure of a narrower range or more specific group in addition to a broader range or larger group is not a disclaimer of the broader range or larger group. All ranges disclosed herein are inclusive of the endpoints, and the endpoints are independently combinable with each other.

The invention claimed is:

1. A method of manufacture of a bisphenol of chemical structure:

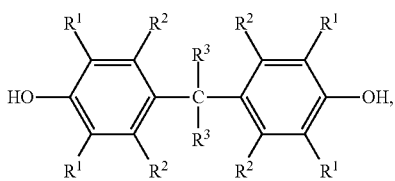

wherein each $R^1$ is independently selected from the group consisting of hydrogen, halogen, methoxy, and $C_{1-12}$ hydrocarbyl provided that the hydrocarbyl group is not tertiary hydrocarbyl; each $R^2$ is independently selected from the group consisting of hydrogen, halogen, and $C_{1-12}$ hydrocarbyl provided that the hydrocarbyl group is not tertiary hydrocarbyl, and each $R^3$ is independently selected from the group consisting of hydrogen, halogen, and $C_{1-11}$ hydrocarbyl, the method comprising:
heating a monohydric phenol of chemical structure:

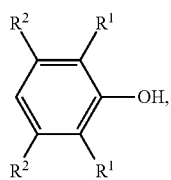

wherein $R^1$ and $R^2$ are as defined above, to a first temperature sufficient to melt the monohydric phenol;
adding a carbonyl compound of chemical structure:

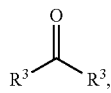

wherein $R^3$ is as defined above, to 2.0 to 2.5 molar equivalents, based on the moles of carbonyl compound, of the monohydric phenol in the presence of catalytic amounts of an organosulfonic acid catalyst and a reaction promoter at a second temperature sufficient to maintain unreacted monohydric phenol in a molten state;
increasing the temperature to a third temperature higher than the second temperature, and mixing for a time sufficient to produce the bisphenol in a yield of 80 to 100%, based on the amount of carbonyl compound;
wherein mineral acids, Lewis acids, and ion exchange resins are not used.

2. The method of claim 1, wherein the monohydric phenol is selected from phenol, 2-methylphenol, 2,6-dimethylphenol, 2,3,6-trimethylphenol, 2-methyl-6-phenylphenol, and combinations thereof.

3. The method of claim 1, wherein the carbonyl compound is formaldehyde, a $C_{2-12}$ aldehyde, or $C_{3-12}$ ketone.

4. The method of claim 1, wherein the carbonyl compound is selected from formaldehyde, acetaldehyde, acetone, cyclohexanone, and combinations thereof.

5. The method of claim 1, wherein the organosulfonic acid catalyst is selected from dodecylbenzene sulfonic acid, ethylbenzene sulfonic acid, butylnaphthalene sulfonic acid, and combinations thereof.

6. The method of claim 1, wherein the reaction promoter is selected from 3-mercaptopropionic acid (3-MPA), 4-mercaptobutyric acid, 2-mercaptoisobutryric acid, 3-mercaptoisobutyric acid, and combinations thereof.

7. The method of claim 1, wherein the carbonyl compound is added below a surface of molten monohydric phenol.

8. The method of claim 1, wherein the organosulfonic acid catalyst is added simultaneously with the carbonyl compound, but as a separate stream.

9. The method of claim 1, wherein the organosulfonic acid comprises, based on the moles of carbonyl compound, 0.05 to 0.4 molar equivalent of dodecylbenzene sulfonic acid and the reaction promoter comprises 0.03 to 0.2 molar equivalent of 3-mercaptopropionic acid.

10. The method of claim 1, wherein each occurrence of $R^1$ and $R^3$ is methyl, and each occurrence of $R^2$ is hydrogen.

11. The method of claim 1, wherein the bisphenol is of chemical structure:

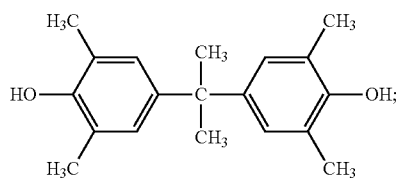

and
wherein the method comprises:
addition of acetone to 2.0 to 2.5 molar equivalents of 2,6-dimethylphenol in the presence of catalytic amounts of an organosulfonic acid catalyst and a reaction promoter at a second temperature of 40 to 50° C.; and
increasing the temperature to a third temperature of 70 to 80° C. and mixing.

12. The method of claim 11, wherein the adding is done for 3 to 6 hours; and
the mixing is done for 18 to 36 hours.

* * * * *